United States Patent [19]

Curtin

[11] 4,173,980
[45] Nov. 13, 1979

[54] CORNEAL RESURFACING APPARATUS AND METHOD

[76] Inventor: Brian J. Curtin, 32 E. 64th St., New York, N.Y. 10021

[21] Appl. No.: 771,942

[22] Filed: Feb. 25, 1977

[51] Int. Cl.² .............................................. A61B 17/00
[52] U.S. Cl. ................................................. 128/303 R
[58] Field of Search ............... 128/303 B, 303 R, 304, 128/305, 312, 355, 76.5, 2 T; 351/5, 13

[56] References Cited

U.S. PATENT DOCUMENTS

| 3,172,404 | 3/1965 | Copenhaver et al. | 128/76.5 |
| 3,369,548 | 2/1968 | Moore et al. | 128/303 R |
| 3,976,077 | 8/1976 | Kerfoot, Jr. | 128/305 |

FOREIGN PATENT DOCUMENTS 2311257  9/1974 Fed. Rep. of Germany ...... 128/303 R

OTHER PUBLICATIONS

Ainsle, "Corneal Grafting", New York, Appleton-Century-Crofts, pp. 207-218.
Mueller, et al., "Experimental Eye Research", vol. 6, 1967, pp. 42-47.
Straatsma, et al., "Archives of Ophthalmology", vol. 88, Sep. 1972, pp. 325-329.

Primary Examiner—William E. Kamm
Attorney, Agent, or Firm—Ostrolenk, Faber, Gerb & Soffen

[57] ABSTRACT

Apparatus for abrading the anterior surface of the cornea, including a headrest to hold the patient's head stationary, means for fixing the eye whose cornea is to be surfaced, a grinding lap or disc for grinding the corneal surface, means for positioning the grinding disc over the eye and means for controlling the motion of the grinding disc for grinding the corneal surface to the desired extent and in the desired shape; a method for resurfacing the cornea is also disclosed, wherein the functions of the various means described above are herein realized.

40 Claims, 4 Drawing Figures

CORNEAL RESURFACING APPARATUS AND METHOD

BACKGROUND OF THE INVENTION

The invention relates to a corneal resurfacing apparatus. It has application to the cornea of any eye, but would typically be used on the human eye.

The refractive power of the cornea may be changed by altering the curvature of its anterior surface. For example, nearsightedness, farsightedness and/or astigmatism and other eye focusing problems can be adjusted by reshaping the cornea. Contact lenses seated on the cornea adjust visual acuity by reshaping the cornea. However, where contact lenses temporarily alter the anterior corneal curvature while they are being worn, the apparatus of the invention has as its purpose the permanent alteration of this curvature.

The concept of grinding the anterior corneal surface to alter its curvature is disclosed, for example, in Mueller and O'Neill, "Some Experiments on Corneal Grinding", which appeared in *Experimental Eye Research* (1967), 6, 42–47, a paper published by two researches in London, England. However, an apparatus for corneal resurfacing or grinding was not proposed by these researchers or by other prior art of which I am aware.

A rotating grinding disc which rotates around a single axis and is held stationary over the surface that it is grinding does not produce an evenly ground depression. Instead, the depression produced by such a disc has a uniform annular maximum depression toward its periphery and a gradually shallower annular depression moving toward its center. This results from the geometry of the disc, as more abrasive material passes over a particular location toward the periphery of the disc than toward the center of the disc in each revolution of the disc. To achieve a more uniform grinding depression, the Mueller and O'Neill article proposes providing a grinding lap which simultaneously rotates around two mutually perpendicular axes, one generally along the visual axis of the eye and the other perpendicular to the visual axis.

But, a corneal resurfacing apparatus requires more than a grinding lap. The patient's head must be held stationary as his cornea is being ground. Furthermore, the eyeball readily shifts in its socket and it could be quite harmful if such shifting occurs while the cornea is being ground. Further, in order that the grinding program might be accurately followed and that the cornea be properly surfaced, the eye must be precisely and properly aligned and its visual or optical axis must be properly aligned with respect to the placement of the grinding disc. Finally, as the cornea is quite thin and as the grinding must be done with great precision, the grinding program must be controlled and must grind only to a predetermined depth.

Other techniques are known for correcting refractive errors of the cornea. These have involved incisions in the cornea, or knife cutting away of part of the cornea to alter its shape or to temporarily remove that part of the cornea to work on it and then replace it in the eye, or replacement of part of the cornea with some substitute, etc. See for example, Sato, T. (1953) Am. J. Opthal. 36:823; Barraquer, J. I. (1964) Archos Soc. Am. Oftal. Optom. 5:27 and (1968) J. Cryosurg. 1:39; Ainslie, D. (1969) Trans. Opthal. Soc. U. K. 89:647; Littman, H. (1967) Archos Soc. Am. Oftal. Optom. 6:103; Krawicz (1964) Am. J. Opthal. 57:828 and (1965) Klinoczna 35:13. But, none of these techniques so closely controls the shape of the anterior surface of the cornea as the present invention.

SUMMARY OF THE INVENTION

Accordingly, it is the primary object of the present invention to provide an apparatus for permanently altering the anterior surface of the cornea of an eye.

It is another object of the invention to provide a method for permanent alteration of the curvature of the anterior surface of the cornea.

It is yet another object of the invention to provide such an apparatus, wherein the cornea is resurfaced or abraded in a particular predictable manner.

It is a further object of the invention to ensure precise placement and orientation of the eye whose cornea is being resurfaced.

It is a further object of the invention to provide apparatus for resurfacing the cornea in a precise programmed manner.

It is yet a further object of the invention to provide a method for resurfacing the cornea in accordance with the foregoing objects.

These and other objects and advantages of the invention will become apparent from the following description of the invention and description of preferred embodiments thereof.

A corneal resurfacing apparatus according to the invention can comprise means for holding the head of the patient stationary and comprises means for fixing the eye whose cornea is to be surfaced, a corneal resurfacing unit comprising a grinding disc or grinding lap or other grinding means, means for driving the grinding means and means for positioning the grinding means over the eye and for controlling its movement over the cornea. Additionally, there may be means for aligning or orienting the eye so that its optical or visual axis extends in a particular direction, that the grinding program will properly surface the cornea.

A headrest holds the patient's head stationary. This headrest could include head clamping or securing means for preventing the head from shifting.

Located above the eye to be treated is the ocular fixation unit. It is movable into position over the eye once the head is held stationary. The ocular fixation unit is moved into engagement with the eyeball and holds the same stationary. One example of an ocular fixation unit is an annular circumcorneal suction ring which secures itself to the eyeball and leaves a large open area in its center where the cornea to be resurfaced is accessible.

For properly aligning and orienting the eye, a viewing target may be supported in front of the eye. The patient focuses on the target, and in doing so, he aligns his eye correctly. A sighting telescope may be associated with the target so that the operator of the corneal resurfacing apparatus can ensure that as the ocular fixation unit is being emplaced while the patient is focusing on the target, the patient's optical or visual axis is aligned on the target.

The corneal resurfacing unit is movable into position over the cornea once the eye has been fixed. The sighting device could be used to properly place the resurfacing unit and particularly its grinding disc or lap for the start of the grinding program. For ensuring proper grinding, fine adjustments are made in the position of the grinding lap to ensure that it is properly placed both across the surface of the cornea and starting just at the surface of the cornea.

The grinding disc or grinding lap may take many different forms and appropriate means will be provided for controlling the pathway traveled by the grinding lap or disc. Various techniques of doing this are described in the description of the preferred embodiments, but other techniques will be apparent to those skilled in the art.

Finally, the depth of the grinding of the cornea must be closely controlled and can either be part of the grinding or resurfacing program or a separate depth metering means may be associated with the grinding lap or disc.

The invention will be better understood from the following detailed description taken in conjunction with the accompanying drawings.

DESCRIPTION OF THE PREFERRED EMBODIMENTS

Figure 1:
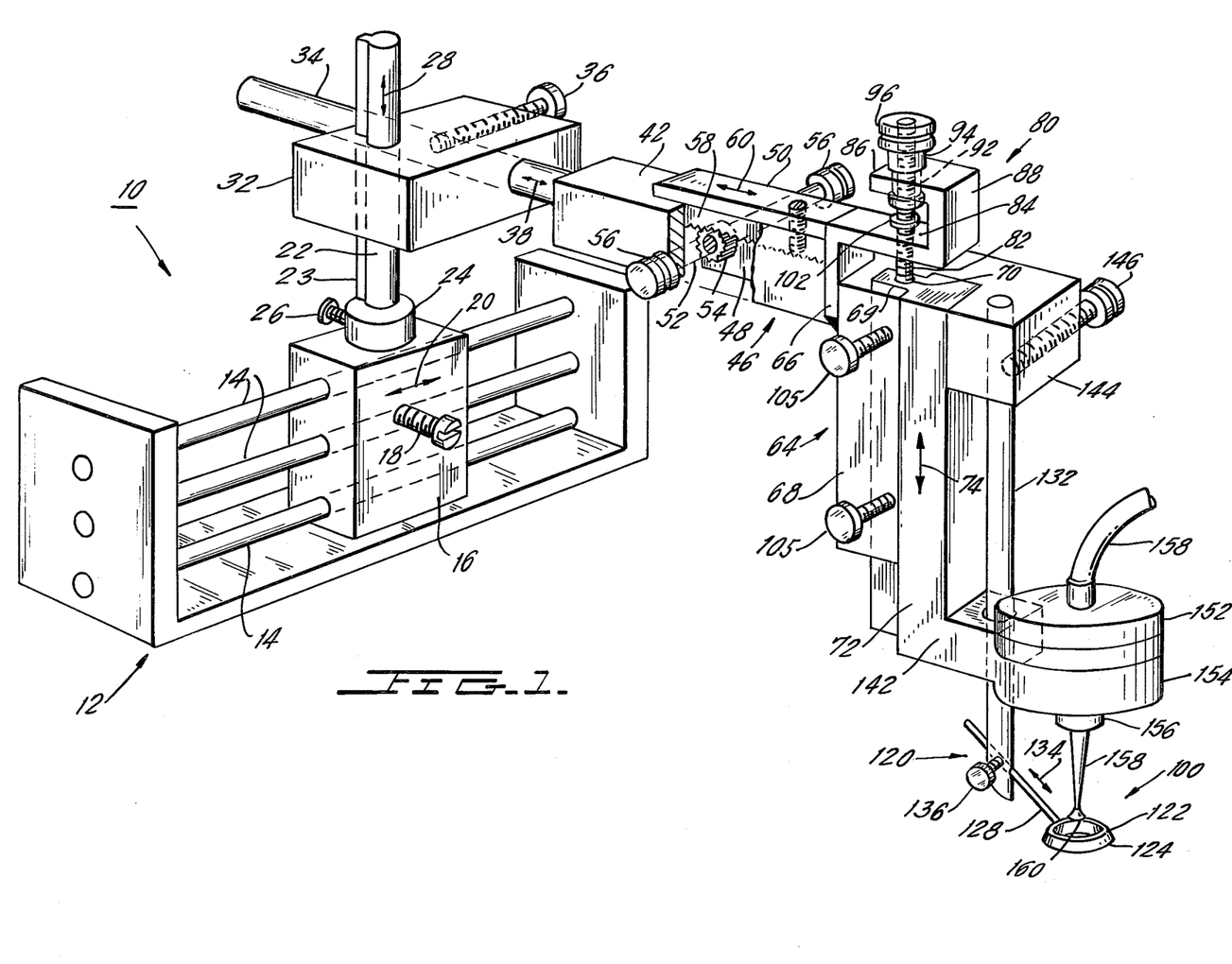
FIG. 1 is a perspective view of one embodiment of a corneal surfacing apparatus incorporating the invention.
Figure 2:
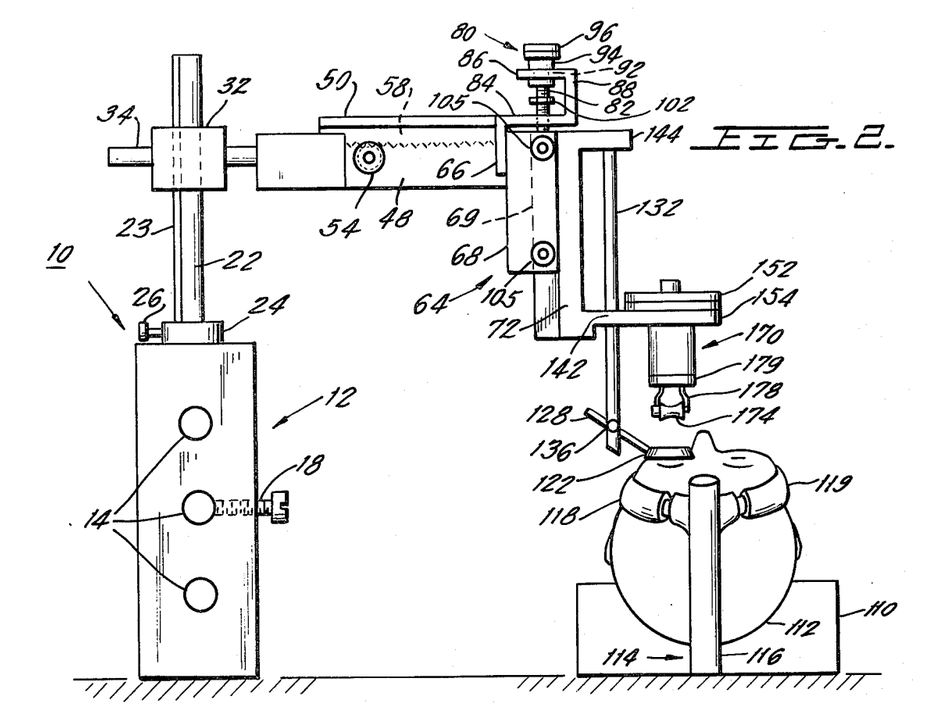
FIG. 2 is an elevational view of the second embodiment of such apparatus in use.

With reference to FIGS. 1 and 2 which show the first and second embodiments of the invention, all elements in both embodiments are the same, except for the grinding means, whereby the following description will apply to both of these embodiments. The corneal resurfacing apparatus 10 includes means for positioning the patient's eye for resurfacing, for holding the eyeball in place, for grinding the anterior surface of the cornea and for moving the grinding means over the cornea to position it for grinding.

The apparatus includes the stand 12 which is the support for the major components of the apparatus. As shown in FIG. 2, the stand 12 seats on or is attached to a supporting surface. In particular, the stand 12 supports the below described grinding means 100 of FIG. 1 or 170 of FIG. 2. The various elements shown in FIGS. 1 and 2 between the stand 12 and the grinding means 100 are for the purpose of positioning the grinding means at the proper location. The stand 12 includes the grinding bars 14. The guiding bars pass through support block 16 which is slidable along the bars 14. The set screws 18 is tightened to hold the block 16 at any desired location along the bars 14. In this manner, the initial position of the grinding means 100 along the pathway of the arrows 20 is determined. The post 22 extends into a receiving opening in the block 16. Both the post 22 and the opening in the block are keyed as at 23 to prevent grinding means 100 from swiveling around post 22. At the top of the receiving opening in the block is located the collar 24 with a threaded aperture to receive the set screw 26. Once the height of the post 22 with respect to the block 16 along the pathway indicated by the arrows 28 is determined, set screw 26 is tightened.

There is securely fastened to the shaft 22 the support block 32. A horizontally extending shaft 34 passes through a receiving bore in the block 32. The shaft 34 is longitudinally shiftable through the block 32. The set screw 36 passes through a threaded receiving bore in the block 32 and is tightened against the shaft 34 to secure the same at a desired longitudinal position with respect to the block 32. This makes an initial adjustment in the position of the shaft 34 with respect to the block 32.

The foregoing gross adjustments are not enough. Close adjustment of the position of the grinding means 100 is necessary because each person's head is a different size and it might be slightly differently placed on the below described headrest. Further, it may be the patient's left or right eye that is to be resurfaced.

Fastened to one end of the shaft 34 is the block 42 which is moved along the pathway indicated by the arrows 38 upon corresponding shifting of the shaft 34 with respect to the block 32. Block 42 is connected with a two part assembly 46 which includes the lower block portion 48 which is secured to and movable with the block 42 and the upper horizontally shiftable section 50. A shaft 52 having a pinion gear 54 secured thereto passes through a bore in the lower block 48. The pinion gear 54 is freely rotated by rotation of the shaft 52. Rotation knob 56 at the end of the shaft 52 enables its rotation. The assembly section 50 has a depending toothed rack beneath it which meshes with the teeth of the gear 54. Upon rotation of the knob 56, the entire section 50 is moved along the pathway indicated by the arrows 60. Rotation of the knob 56 gives a fine horizontal position adjustment to the grinding means 100.

There is rigidly secured to the assembly section 50 the support means 64 for the grinding means 100. The support means 64 includes the supporting plate 66 which at one side is attached to the assembly section 50 for being horizontally moved therewith. To the other side of the plate 66 is secured the base support block 68. The base support block 68 is notched at 69 at its other side. Notch 69 receives a correspondingly shaped tongue 70 on the grinding means support block 72. The grinding means support block 72 is vertically shiftable along the pathway indicated by arrows 74 with respect to the base support block 68.

There is affixed to the grinding means support block 72 a fine adjustment means 80 for setting and resetting the initial height of the grinding means 100 and the depth to which the cornea of the eye is ground by the grinding means 100. The fine vertical height adjustment means comprises the screw threaded shaft 82 which is affixed immovably to and projects from the top of the tongue 70 of the block 72. The surface of the shaft 82 is threaded with a very fine screw thread. The previously mentioned frame support element 66 which is permanently attached to the horizontally shiftable element 50 has a "C" shaped upper portion including the lower leg 84, the spaced away upper leg 86 and the joining vertical web 88. The lower leg 84 has a clearance opening therethrough through which the shaft 82 passes.

In the upper leg 86 is an opening 92 which receives a guide sleeve 94 therein. The interior of the sleeve 94 is correspondingly threaded and is of the same diameter as the exterior of the shaft 82. The opening 92 through the support means upper leg 86 is narrower than the external width of the sleeve 94 at both of the top and bottom of the leg 86 so that the sleeve 94 is captured on the leg 86 but is rotatable with respect thereto. A manually operable knob 96 is attached at the top of the sleeve 94 such that rotation of the knob 96 rotates the sleeve. Rotation of the sleeve with respect to the stationary shaft 82 raises and lowers the shaft and thereby the block 72 and the grinding means 100 along the pathway indicated by the arrow 74. The fine screw thread on the shaft 82 ensures that very fine movements of the grinding means can be obtained.

There is a maximum depth to which the grinding means 100 can grind the cornea without causing irreparable damage. Before the grinding means is operated, therefore, this maximum depth setting should be established. A micrometer adjustment ring 102 having a screw threaded interior is carried on the shaft 82 between the legs 84 and 86. Rotation of the ring 102 with respect to the shaft 82 positions that ring along the shaft. The spacing between the lower surface of the ring 102 and the lower leg 84 of the assembly 80 determines the maximum extent to which the shaft 82, block 72 and grinding means 100 can descend into the cornea. Appropriate indicator markings may be applied on the periphery of the ring 102 to calibrate the extent of its rotation, in terms of micrometers of height over which the ring has moved, or the vertical web 88 may be marked to indicate the height of the ring or other appropriate indicator means may be associated with the ring 102 for setting its height above leg 84.

To ensure that the block 72 does not shift vertically as a result of its being moved or pulled during use, the clamping set screws 105 are tightened and hold the block 72 securely with respect to the block 68 following the positioning of the block 72 by means of the assembly 80.

Turning to FIG. 2, the head of the patient must be held stationary when the cornea of his eye is being operated upon. For this purpose, a headrest 110 having a patient's head receiving recess 112 therein is provided. An appropriate clamp 114 holds the patient's head securely in position against any movement in the depression 112. As illustrated, the clamp 114 comprises the post 116, which projects up past the top, center of the head of the patient. Two arms 118, 119 extend from the post and wrap around the forward part of the head of the patient and these arms are adjusted to securely clamp the patient's head in position.

Once the patient's head has been secured in position, the eye to be operated upon must be fixedly secured against movement. Returning to FIG. 1, the securing means 120 is provided for this purpose. It includes a circumcorneal suction ring 122 which is a conventional device known in opthalmic practice. This device includes an annular, hollow ring 124 which has an open bottom side that is applied to the surface of the eyeball around the cornea. The ring 124 is attached and is in communication with a rigid, hollow suction tube 128 which opens into the hollow, open bottomed ring 124. The tube 128 is sufficiently rigid to hold the ring 124 stationary over the eye. The rigid tube 128 passes through a cooperatingly shaped opening in the upstanding support post 132. The position of the tube 128 is adjustable with respect to the post 132 along the pathway indicated by the arrows 134. The shaft 128 and the ring 124 secured thereto can be pivoted around the axis of shaft 128 in the receiving opening in post 132 to any desired tilt orientation. This ensures proper placement of the ring 124 on the eyeball of the patient and with respect to the grinding means 100. A set screw 136 in the post 132 is tightened to secure the tube 128 at a desired position over the eyeball and with respect to the below described grinding element of the grinding means 100.

Before the suction ring 124 is applied to the eyeball of the patient, the annular ring 124 is held just over the patient's eyeball and the patient looks through the opening in the ring at a target. The target could be the below described grinding disc 160 or any other object set up to be sighted on. The operator of the apparatus locks the ring arrangement 122 on the patient's eye when the patient's visual axis is aligned with the target.

The above identified grinding means support block 72 is generally "C" shaped including a lower leg 142 and an upper leg 144 joined by the main upstanding portion of the block 72.

The upstanding post 132 passes through a clearance guide opening in the lower leg 142 of the block 72 and is movably received in an opening in the upper leg 144 of that block. A set screw 146 is tightened against the shaft 132 to fix the height of the shaft 132 with respect to the height of the block 72, thereby to cooperate in fixing the height of the circumcorneal suction ring 124 over the eyeball.

When suction is applied to the hollow tube 128 (by means not shown) and the bottom of the suction ring 124 is applied to the surface of the eyeball surrounding the cornea, the suction force holds the ring 124 securely to the eyeball without damaging it.

The grinding means 100 includes a housing 152 which seats upon extension 154 at the end of the lower leg 142 of the block 72 and the housing 152 is immovably fixed to the support platform 154. The housing 154 has an air or gas operated turbine (not shown) inside the turbine chamber 156. The hose 158 conducts gas or air to the turbine for spinning it. The turbine spins the support shaft 158 to which the grinding disc 160 is attached. The undersurface of the grinding disc 160 is typically slightly concaved to conform to the curvature of the cornea, as suggested in the enlarged view of the third embodiment in FIG. 4. The disc 160 is smaller in diameter than the cornea to be resurfaced. It is necessary, therefore, that the disc be moved to different locations over the cornea during the course of the grinding program. The above described moving means 46 and 80 move the grinding disc to various locations.

Positioning of the disc 160 over the cornea to be resurfaced requires that the opeator of the apparatus look closely directly at the disc 160 to find its location and readjust its position. In connection with the below described embodiment of FIG. 4, an alternate technique for aiming the grinding disc and the eyeball of the patient is described.

The second embodiment of FIG. 2 differs from the first embodiment only in the grinding means 170. In other respects, the apparatus are the same. The grinding means 170 is shown in greater detail n FIG. 3. It includes the housing 171 which is disposed beneath and immovably on the support platform 154. Disposed at the bottom end of the housing 170 is the corneal grinding lap assembly 175. Assembly 172 is comprised of the grinding lap 174 which is supported on a horizontal axle 176.

Figure 3:
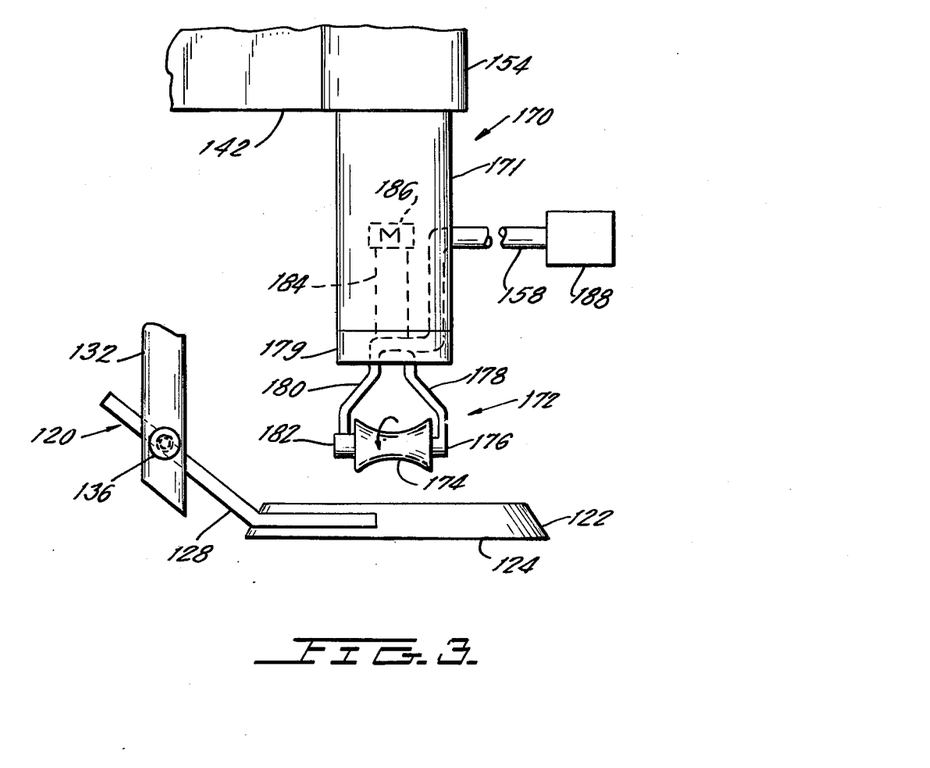
FIG. 3 is a fragmentary, side elevational view of a second embodiment of apparatus incorporating the invention.

The lap 174 is circular in cross-section perpendicular to the axle at any poing along the axle 176. The lap 174 is wider at its ends and narrows toward its center. Motor means are provided to rotate the grinding lap 174 simultaneously around its horizontal axle 176 and also around the vertical axis of the housing 170, which is perpendicular to the horizontal axle 176. The axle 176 at one end is rotatably supported in the rigid strut 178. Strut 178, in turn, passes into the bottom end 179 of the hosing 170. The other end of the axle 176 is rotatably supported in the other strut 180. Strut 180 is a hollow air tube which leads from inside the bottom end 179 of the housing to the conventional air turbine 182. The air turbine 182 is attached to the other end of the axle 176 such that air flowing through the strut 180 activates the air turbine to spin the axle 176 and to spin the grinding lap 174 around that axle.

The bottom end 179 of the housing 171 is an air or gas chamber which communicates with the strut 180 as the strut spins.

The post 184 is supported by a bearing (not shown) inside the housing 170 for rotation therein about the vertical axis of the housing. The post 184 is attached to the struts 178, 180 at the bottom of the housing 170, whereby rotation of the post 184 around the vertical axis also rotates the struts 178, 180 around that axis, and thereby rotates the grinding lap 174 around the vertical axis. A small electric motor 186 on the post 184 drives the post to rotate the grinding lap.

For activating the air turbine 182, an air pump 188 is connected to the air conduit 158 which passes into the housing 171 and connects to the air or gas chamber at the bottom end of the housing 171, and thus the pump 188 communicates with the turbine 182. An appropriate switch (not shown) activates both the motor 186 and the pump 188.

With the above described first and second embodiments of the corneal resurfacing apparatus, the patient's head is first rested on the headrest 110. It is then clamped by the clamps 118, 119. Next, the grinding disc 160 and the ring 124 are moved over the eye so as to align the visual axis with a target. The circumcorneal ring 124 is placed over the eye, and with the eye properly aimed, suction is applied to the circumcorneal ring to secure the eye in position. The grinding disc 160 or lap 174 is moved into position over the eye. Then the cornea is resurfaced.

Figure 4:
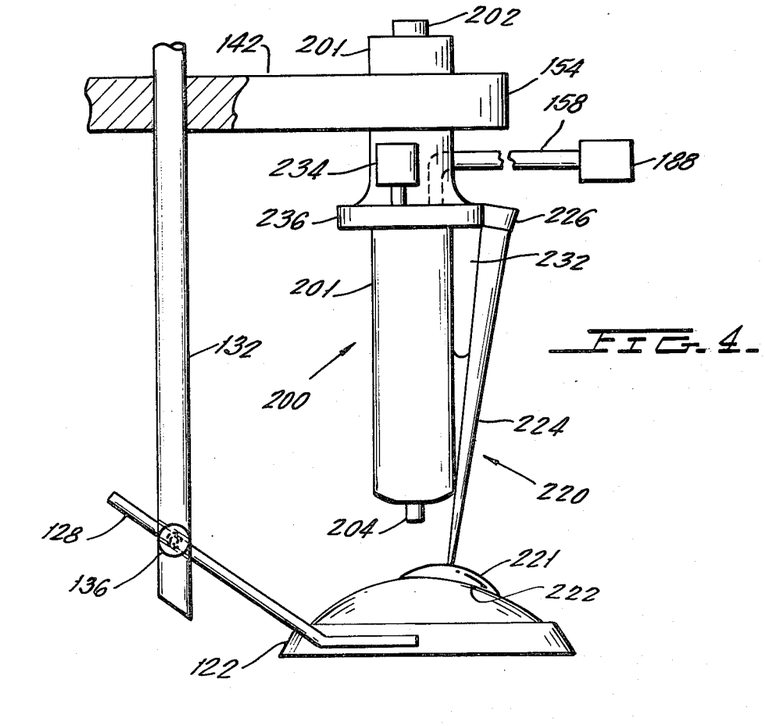
FIG. 4 is a fragmentary side elevational view of a third embodiment of such apparatus incorporating the invention.

In the third embodiment of resurfacing apparatus of FIG. 4, all elements up to the grinding means correspond in construction and function to elements of the first embodiment. These elements are not shown or explained again. Some of the elements located adjacent to or which cooperate with the grinding means also appear, and these have the same function and operation as in the first embodiment and they are identified by the same reference numerals.

In the third embodiment, there is a combined eye aiming device 200 and corneal resurfacing tool 220, which are combined in a single unit. This arrangement has the benefit that the eyeball to be operated upon can be easily and accurately aimed as the resurfacing tool is positioned over the eye. Turning first to the aiming device, it includes a rigid housing 201 which is rigidly and non-movably connected to support block leg 142, 154. Device 200 includes an eyepiece 202 at the upper end of the housing 201 and a viewing lens 204 at the lower end of the housing. The housing 201 is hollow and supports appropriate lenses (not shown) within itself to enable viewing of the patient's eye through the lens 202.

The lens 204 has the additional benefit that it serves as the target on which the patient focuses his attention. The patient's visual axis is thereby aligned with the target while the cornea of his eye is being fixed against movement. This properly aims the cornea for a subsequent grinding program.

One reason why the grinding tool 220 and the aiming device 200 can be combined in a single unit is that the tool 220 is eccentric to the housing 201. In the illustrated embodiment, the tool 220 comprises the rotatable grinding disc 221 whose undersurface 222 is shaped to the curvature that is intended to be produced on the anterior surface of the cornea to be ground. The disc 221 is concentrically supported on a support assembly 224, which includes a drive shaft that spins with the grinding disc 221. At the upper end of the drive shaft is an air or gas operated turbine or motor 226 which rotates the disc 221. The air passageway 158 communicates with the air turbine 226 by means to be described and causes the turbine to spin.

The grinding disc 221, support assembly 224 and turbine 226 are supported eccentrically to the housing 201 by the support block 232 positioned between the support assembly 224 and the housing 201. To uniformly grind the surface of the cornea, the disc 221 cannot spin while remaining in a stationary position. Instead, the entire tool 220 is rotated around the axis of the housing 201. This is accomplished by a motor 234 inside the housing, which is connected with the annular air conductor ring 236 outside the housing 201. The turbine 226 is, in turn, connected to the ring 236. The air passage from pump 158 communicates into the ring 236 and thereby to the turbine 226. The motor 234 rotates the air conductor ring 236 and this, in turn, rotates the air turbine 226 and the attached disc 221 around the axis of the housing 201. Thus, at the same time as the disc 221 is spinning, it is revolving around the vertical axis of the housing 201.

The connection between turbine 226 and ring 236 is flexible to permit variation in the angle between support 224 and housing 201. Such variation is needed to adjust for different radii of curvature that are to be imparted to the anterior surface of the cornea. To account for this, the support block may be reshaped or replaced with one having a different shape, or a cam may be adjustably attached on block 232 for this purpose or other adjustment means may be used.

As a further alternative to the manual repositioning of the grinding disc 160 of the first embodiment, or the two axis rotation of the grinding lap 174 of the second embodiment or the eccentric mounting of the disc 221 and its revolving eccentrically around the axis of the housing 201 of the third embodiment, a grinding element may be provided and appropriate programmed means, perhaps computer programmed, would control the pathway followed by the grinding element or other grinding means, including the boundaries of the surface area of the cornea to be surfaced, the degree to which each section of the cornea is ground, and the depth to which it is ground.

Although preferred embodiments of this invention have been described, many variations and modifications will now be apparent to those skilled in the art, and it is therefore preferred that the present invention be limited not by the specific disclosure herein, but only by the appended claims.

What is claimed is:

1. A corneal resurfacing apparatus comprising:
   a circumcorneal suction ring for fixing the eye whose cornea is to be resurfaced so that the eye does not move as it is being resurfaced and for also stiffening the cornea; means connected with said suction ring for transmitting suction thereto, means for moving said suction ring into engagement with the eyeball whose cornea is to be resurfaced;

a grinding element for being moved into contact with the anterior corneal surface of the eye whose cornea is to be resurfaced, and said grinding element being comprised of a material adapted for grinding the corneal surface;

means for positioning said grinding element over the anterior corneal surface;

means for moving said grinding element to grind the corneal surface; means for controlling the manner and extent to which said grinding element grinds the corneal surface for grinding the corneal surface to define an optical surface.

2. The corneal resurfacing apparatus of claim 1, further comprising means for clamping the head having the eye whose cornea is being resurfaced against movement with respect to said corneal resurfacing apparatus.

3. The corneal resurfacing apparatus of claim 1, further comprising means for aiming the eye whose cornea is to be resurfaced, prior to the fixing of the eye by said fixing means.

4. The corneal resurfacing apparatus of claim 3, wherein said aiming means comprises a viewable target placed to be viewed by the eye whose cornea is to be resurfaced.

5. The corneal resurfacing apparatus of claim 4, wherein said aiming means further comprises a telescope which is aimed at the eye whose cornea is being resurfaced and said telescope being adapted and aimable for viewing of that eye.

6. The corneal resurfacing apparatus of claim 3, wherein said aiming means further comprises a telescope which is aimed at the eye whose cornea is being resurfaced and said telescope being adapted and aimable for viewing of that eye.

7. The corneal resurfacing apparatus of claim 6, further comprising a headrest for positioning the head of the person having the eye whose cornea is to be resurfaced.

8. The corneal resurfacing apparatus of claim 6, further comprising a stand to which said eye fixing means, said grinding element and said grinding element positioning means are attached and on which they are supported.

9. The corneal resurfacing apparatus of claim 8, wherein said aiming means further comprises a viewable target placed to be viewed by the eye whose cornea is to be resurfaced; said aiming device being attached to and supported on said stand.

10. The corneal resurfacing apparatus of claim 8, further comprising a headrest for positioning the head of the person having the eye whose cornea is to be resurfaced; said headrest being attached to and supported by said stand.

11. The corneal resurfacing apparatus of claim 1, further comprising a stand to which said eye fixing means, said grinding element and said grinding element positioningmeans are attached and on which they are supported.

12. The corneal resurfacing apparatus of claim 11, further comprising eye fixing means position adjustment means between said stand and said eye fixing means for enabling adjustment of the position of said eye fixing means over the eye having the cornea to be resurfaced; and said grinding element positioning means being between said stand and said grinding element for enabling adjustment of the position of said grinding element over the eye having the cornea to be resurfaced.

13. The corneal resurfacing apparatus of claim 12, wherein said grinding element positioning means comprise vertical position adjustment means between said grinding element and said stand for adjusting the vertical position of said grinding element with respect to said stand and horizontal position adjustment means between said grinding element and said stand for adjusting the horizontal position of said grinding element with respect to said stand, thereby to enable positioning of said grinding element over the eye whose cornea is to be resurfaced.

14. The corneal resurfacing apparatus of claim 13, further comprising means for limiting the maximum extent of vertical movement of said grinding element toward the eye having the cornea being resurfaced.

15. The corneal resurfacing apparatus of claim 12, wherein said eye fixing means position adjustment means comprises first vertical position adjustment means between said eye fixing means and said stand for adjusting the first vertical position of said eye fixing means with respect to said stand; first horizontal position adjustment means between said eye fixing means and said stand for adjusting the first horizontal position of said eye fixing means with respect to said stand; and first rotational position adjustment means for adjusting the rotational position of said eye fixing means around and with respect to said stand, thereby to enable positioning of said eye fixing means over the eye whose cornea is to be resurfaced.

16. The corneal resurfacing apparatus of claim 15, wherein said grinding element position adjustment means comprises second vertical position adjustment means between said grinding element and said stand for adjusting the vertical position of said grinding element with respect to said stand and second horizontal position adjustment means between said grinding element and said stand for adjusting the horizontal position of said grinding element with respect to said stand, thereby to enable positioning of said grinding element over the eye whose cornea is to be resurfaced.

17. The corneal resurfacing apparatus of claim 16, further comprising a headrest for positioning the head of the person having the eye whose cornea is to be resurfaced; said headrest being attached to said stand.

18. The corneal resurfacing apparatus of claim 17, further comprising means for clamping the head having the eye whose cornea is to be resurfaced against movement with respect to said headrest.

19. The corneal resurfacing apparatus of claim 1, wherein said grinding element moving means comprises a motor means for rotating said grinding element.

20. The corneal resurfacing apparatus of claim 19, wherein said grinding element moving means further comprises an axle on which said grinding element is supported and around which said grinding element rotates; said grinding element axle being oriented transversely to the visual axis of the eye whose cornea is to be resurfaced; a post that is generally alignable with the visual axis of the eye whose cornea is to be resurfaced; said grinding element axle being supported on and being rotatable around said post, whereby said grinding element is simultaneously rotatable about two axes, that of said axle and that of said post;

first rotation means for rotating said axle around said post; second rotation means for rotating said grinding element around said axle.

21. The corneal resurfacing apparatus of claim 20, further comprising a stand to which said eye fixing means and said grinding element are attached and on which they are supported; said post also being connected to said stand to be supported thereby.

22. The corneal resurfacing apparatus of claim 20, wherein said grinding element has a surface which contacts the cornea being resurfaced and said grinding element surface being shaped so as to define a desired shape for the corneal surface upon grinding it.

23. The corneal resurfacing apparatus of claim 20, wherein said second rotation means comprises an air turbine attached to said grinding element; air flow transmitting means communicating with said air turbine for spinning same and thereby rotating said grinding element around said axle.

24. The corneal resurfacing apparatus of claim 19, wherein said grinding element is supported on a grinding element support and said grinding element rotates around its said support; means for rotating said grinding element around its said support; a grinding element supporting housing; means for holding said grinding element supporting housing stationary with respect to the eye whose cornea is being resurfaced; said grinding element being supported on its said supporting housing and its said support being moved all around its said supporting housing, thereby to position said grinding element at different locations around the cornea being resurfaced.

25. The corneal resurfacing apparatus of claim 24, wherein said grinding element has a surface which contacts the cornea being resurfaced and said grinding element surface being shaped so as to defined a desired shape for the corneal surface upon grinding it.

26. The corneal resurfacing apparatus of claim 24, wherein said grinding element rotation means comprises an air turbine attached to said grinding element; air flow transmitting means communicating with said air turbine for spinning same and thereby rotating said grinding element around its said support.

27. The corneal resurfacing apparatus of claim 24, further comprising means for aiming the eye whose cornea is to be resurfaced prior to the fixing of the eye by said fixing means.

28. The corneal resurfacing apparatus of claim 27, wherein said aiming device is located in said supporting housing and said aiming device includes a viewing means for viewing the eye whose cornea is to be resurfaced, and said viewing means facing a direction that is toward the eye whose cornea is to be resurfaced when that eye is in position to have its cornea resurfaced.

29. The corneal resurfacing apparatus of claim 28, wherein said aiming device comprises a viewable target placed to be viewed by the person having the eye whose cornea is to be resurfaced.

30. A method for resurfacing the cornea of an eye, comprising the steps of:
aiming the eye whose cornea is to be surfaced so that the visual axis of the eye extends in a particular direction;
fixing the position and orientation of the eye after the eye has been aimed; simultaneously stiffening the cornea so that it may be ground without deforming;
moving a corneal grinding element onto the cornea of the eye and grinding that cornea to define an optical surface.

31. The method for resurfacing the cornea of an eye of claim 30, wherein the cornea is ground to a predetermined limited depth.

32. The method for resurfacing the cornea of an eye of claim 30, further comprising moving a grinding element over the cornea being resurfaced in a manner to avoid non-uniform grinding by the grinding element at any particular area of the cornea being resurfaced.

33. The method for resurfacing the cornea of an eye of claim 30, further comprising before the step of aiming the eye, fixing the head having the eye whose cornea is to be resurfaced at a fixed orientation and position.

34. The method for resurfacing the cornea of an eye of claim 30, wherein the step of fixing the position and orientation of the eye comprises applying a circumcorneal suction ring to the eye and applying suction to the ring.

35. A corneal resurfacing apparatus comprising:
means for fixing the eye whose cornea is to be resurfaced so that the eye does not move as it is being resurfaced and for also stiffening the cornea so that it may be ground without deforming;
a grinding element for being moved into contact with the anterior corneal surface of the eye whose cornea is to be resurfaced, and said grinding element being comprised of a material adapted for grinding the corneal surface;
means for positioning said grinding element over the anterior corneal surface;
means for moving said grinding element to grind the corneal surface; means for controlling the manner and extent to which said grinding element grinds the corneal surface of grinding the corneal surface to define an optical surface.

36. A corneal resurfacing apparatus comprising:
means for fixing the eye whose cornea is to be resurfaced so that the eye does not move as it is being resurfaced;
a grinding element for being moved into contact with the anterior corneal surface of the eye whose cornea is to be resurfaced, and said grinding element being comprised of a material adapted for grinding the corneal surface; said grinding element having a surface which contacts the cornea being resurfaced and said grinding element surface being shaped so as to define an optical surface for the corneal surface upon grinding it;
means for positioning said grinding element over the anterior corneal surface;
means for moving said grinding element to grind the corneal surface; said grinding element moving means comprises:
motor means for rotating said grinding element;
an axle on which said grinding element is supported and around which said grinding element rotates; said grinding element axle being oriented transversely to the visual axis of the eye whose cornea is to be resurfaced; a post that is generally alignable with the visual axis of the eye whose cornea is to be resurfaced; said grinding element axle being supported on and being rotatable around said post, whereby said grinding element is simultaneously rotatable about two axes, that of said axle and that of said post;

first rotation means for rotating said axle around said post;

second rotation means for rotating said grinding element around said axle; said second rotation means comprises an air turbine attached to said grinding element; air flow transmitting means communicating with said air turbine for spinning same and thereby rotating said grinding element around said axle;

means for controlling the manner and extent to which said grinding element grinds the corneal surface for grinding the corneal surface to define an optical surface.

37. The corneal resurfacing apparatus of claim 36, further comprising a stand to which said eye fixing means and said grinding element are attached and on which they are supported; said post also being connected to said stand to be supported thereby.

38. A corneal resurfacing apparatus comprising:

means for fixing the eye whose cornea is to be resurfaced so that the eye does not move as it is being resurfaced;

a grinding element for being moved into contact with the anterior corneal surface of the eye whose cornea is to be resurfaced, and said grinding element being comprised of a material adapted for grinding the corneal surface; said grinding element having a surface which contacts the cornea being resurfaced and said grinding element surface being shaped so as to define an optical surface for the corneal surface upon grinding it;

means for positioning said grinding element over the anterior corneal surface; said positioning means comprising a grinding element support on which said grinding element is supported and said grinding element rotates around its said support; a grinding element supporting housing; means for holding said grinding element supporting housing stationary with respect to the eye whose cornea is being resurfaced; said grinding element being supported on its said supporting housing and its said support being moved all around its said supporting housing, thereby to position said grinding element at different locations around the cornea being resurfaced;

means for rotating said grinding element around its said support for moving said grinding element to grind the corneal surface; said grinding element rotation means comprises an air turbine attached to said grinding element; air flow transmitting means communicating with said air turbine for spinning same and thereby rotating said grinding element around its said support;

means for controlling the manner and extent to which said grinding element grinds the corneal surface for grinding the corneal surface to define an optical surface.

39. A method for resurfacing the cornea of an eye, comprising the steps of:

aiming the eye whose cornea is to be surfaced so that the visual axis of the eye extends in a particular direction;

fixing the position and orientation of the eye after the eye has been aimed by applying a circumcorneal suction ring to the cornea and applying suction thereto, which also stiffens the cornea;

moving a corneal grinding element onto the anterior corneal surface of the eye and grinding that corneal surface to define an optical surface.

40. The method for resurfacing the cornea of an eye of claim 39, further comprising before the step of aiming the eye, fixing the head having the eye whose cornea is to be resurfaced at a fixed orientation and position.

* * * * *